United States Patent
Benecke et al.

(10) Patent No.: US 10,731,105 B2
(45) Date of Patent: Aug. 4, 2020

(54) METHODS AND COMPOSITIONS FOR PREPARING TRIGLYCERIDES CONTAINING FATTY ACID VICINAL DIESTER FUNCTIONALITY

(71) Applicant: Battelle Memorial Institute, Columbus, OH (US)

(72) Inventors: Herman P. Benecke, Columbus, OH (US); Daniel B. Garbark, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 147 days.

(21) Appl. No.: 15/578,600

(22) PCT Filed: May 31, 2016

(86) PCT No.: PCT/US2016/035016
§ 371 (c)(1),
(2) Date: Nov. 30, 2017

(87) PCT Pub. No.: WO2016/196466
PCT Pub. Date: Dec. 8, 2016

(65) Prior Publication Data
US 2018/0216028 A1 Aug. 2, 2018

Related U.S. Application Data

(60) Provisional application No. 62/185,168, filed on Jun. 26, 2015, provisional application No. 62/168,731, filed on May 30, 2015.

(51) Int. Cl.
*C11C 3/08* (2006.01)
*C07C 67/26* (2006.01)
*C07C 67/08* (2006.01)
*C07C 59/40* (2006.01)
*C10M 109/02* (2006.01)
*C10M 105/38* (2006.01)
*C10M 105/36* (2006.01)
*C10N 20/02* (2006.01)
*C10N 30/02* (2006.01)
*C10N 40/08* (2006.01)
*C10N 40/20* (2006.01)
*C10N 40/00* (2006.01)
*C10N 50/10* (2006.01)

(52) U.S. Cl.
CPC .............. *C11C 3/08* (2013.01); *C07C 59/40* (2013.01); *C07C 67/08* (2013.01); *C07C 67/26* (2013.01); *C10M 105/36* (2013.01); *C10M 105/38* (2013.01); *C10M 109/02* (2013.01); *C10M 2207/2835* (2013.01); *C10M 2207/401* (2013.01); *C10N 2020/02* (2013.01); *C10N 2030/02* (2013.01); *C10N 2040/08* (2013.01); *C10N 2040/20* (2013.01); *C10N 2040/40* (2020.05); *C10N 2050/10* (2013.01)

(58) Field of Classification Search
CPC ..... C11C 3/08; C10M 109/02; C10M 105/38; C10M 105/36; C10M 2207/2835; C10M 2207/401; C07C 67/26; C07C 59/40; C07C 67/08; C10N 2220/022; C10N 2250/10; C10N 2240/40; C10N 2240/10; C10N 2240/08; C10N 2230/02
See application file for complete search history.

(56) References Cited

U.S. PATENT DOCUMENTS

| | | |
|---|---|---|
| 6,583,302 B1 | 6/2003 | Erhan et al. |
| 2004/0258635 A1 | 12/2004 | Harry-O'kuru |
| 2012/0129746 A1* | 5/2012 | Benecke ............. C10M 105/42 508/501 |
| 2013/0211033 A1 | 8/2013 | Casciato et al. |

FOREIGN PATENT DOCUMENTS

WO 2006020716 A1 2/2006

OTHER PUBLICATIONS

Supplemental Partial European Search Report for corresponding European application No. EP 16 80 4226, dated Dec. 12, 2018.
Trant, John F., et al., Ring-Opening of Hindered Cyclic Epoxides with Potassium Carboxylates in the Presence of Conjugate Acids, Can. J. Chem 91: 1179-1185 (2013).
Iranpoor, N., et al., Ring Opening of Epoxides with Carboxylates and Phenoxides in Micellar Media Catalyzed with Ce(OTf)4, Synth. Commun. 32 (2002) 15, 2287-2293.
Glueck, Silvia M., et al., Biocatalytic Asymmetric Rearrangement of a Methylene-Interrupted Bis-Epoxide: Simultaneous Control of Four Asymetric Centers Through a Biomimetic Reaction Cascade, Chem. Eur. J. 2004, 10, 3467-3478.
Piazza, George J., et al., Hydrolysis of Mono- and Diepoxyoctadecanoates by Alumina, JAOCS, vol. 80, No. 9. (2003), 901-904.
Cuyamendous, C., et al., Synthesis and Discovery of Phytofurans: Metabolites of α-Linolenic Acid Peroxidation, Chem. Commun., 2015, 15, 15696-15699.
Funk, Timothy W., Enantioselective Synthesis of 5-epi-Citreoviral Using Ruthenium-Catalyzed Asymmetric Ring-Closing Metathesis, American Chemical Society, Organic Letters, 2009, vol. 11, No. 21, 4998-5001.

(Continued)

*Primary Examiner* — Taiwo Oladapo
(74) *Attorney, Agent, or Firm* — Greer, Burns & Crain Ltd.

(57) ABSTRACT

A method for producing a triglyceride including fatty acids with vicinal diesters: (a) providing a triglyceride including fatty acids with epoxide groups; (b) reacting the epoxide groups with carboxylic acid salts under basic conditions to produce a triglyceride including fatty acids with vicinal ester/alkoxides; (c) protonating the vicinal ester/alkoxides to produce a triglyceride including fatty acids with vicinal ester/alcohols; and (d) reacting the vicinal ester/alcohols with carboxylic acids under acidic conditions to produce a triglyceride including fatty acids with vicinal diesters.

9 Claims, No Drawings

(56) References Cited

OTHER PUBLICATIONS

Capon, Robert J., et al., Acid-Mediated Conversion of Methylene-Interrupted Bisepoxides to Tetrahydrofurans: A Biomimetic Transformation, J. Org. Chem., 1998, 63, 75-83.
International Search Report for PCT/US16/35016, dated Oct. 18, 2016.
Written Opinion of the International Searching Authority from corresponding PCT application No. PCT/US2016/035016, dated Oct. 18, 2016.
International Preliminary Report on Patentability from corresponding PCT application No. PCT/US2016/035016, dated Dec. 5, 2017.

* cited by examiner

METHODS AND COMPOSITIONS FOR PREPARING TRIGLYCERIDES CONTAINING FATTY ACID VICINAL DIESTER FUNCTIONALITY

BACKGROUND OF THE INVENTION

This application is a U.S. National Phase under 35 U.S.C. § 371 of International Application No. PCT/US16/35016, filed May 31, 2016, which claims the benefit of U.S. Provisional Application No. 62/185,168, filed Jun. 26, 2015, and U.S. Provisional Application No. 62/168,731, filed May 30, 2015.

This invention relates in general to methods and fatty acid compositions for preparing triglycerides, and in particular for preparing triglycerides containing fatty acid diester functionality.

A number of different products are prepared from oils, including lubricants and other industrial fluids. Many of these products have traditionally been prepared from mineral based oils derived from petroleum. However, in recent years, there has been great interest in using oils derived from renewable feedstocks, including vegetable oils, algal oils and animal oils. The use of oils from renewable feedstocks is desirable to help reduce the world dependence on petroleum and other fossil-derived hydrocarbons. Moreover, these oils are typically biodegradable, which helps reduce the introduction of waste into the environment. Products produced from these oils may also have improved properties.

Triglycerides, also known as triacylglycerols or triacylglycerides, are the major component of oils derived from plants, algae and animals. A triglyceride is a compound consisting of three fatty acids esterified to a glycerol. The fatty acids may differ in length and may be saturated (no carbon-carbon double bonds), mono-unsaturated (one carbon-carbon double bond), di-unsaturated (two carbon-carbon double bonds) or tri-unsaturated (three carbon-carbon double bonds). Individual oils contain characteristic quantities of individual fatty acids that are randomly distributed among the triglyceride structures. For example, a typical soybean oil contains about 11% palmitic acid, 4% stearic acid (both saturated), 54% linoleic acid (di-unsaturated), 23% oleic acid (mono-unsaturated) and 8% linolenic acid (tri-unsaturated).

Whereas oils from renewable resources often have properties making them useful for preparing a variety of products, they also are very susceptible to air oxidation due to the oxidation of methylene groups adjacent to double bonds in their unsaturated fatty acids. These "allylic" methylene groups that are flanked by two double bonds (termed doubly allylic methylene groups) as found in linoleic and linolenic acids are especially prone to oxidation. Previous work (U.S. Pat. No. 8,357,643 and US patent application 2012/0129746) demonstrated that attachment of two ester groups to the original doubly bonded carbon atom in these fatty acid esters significantly reduces the oxidative susceptibility of their allylic methylene groups. This functionality in modified fatty acids is referred to as vicinal diester functionality or simply vicinal diesters.

An efficient method to prepare vicinal diesters in fatty acid esters is to first epoxidize all fatty acid double bonds and then react these epoxide groups with carboxylic acid anhydrides under basic conditions. However, the cost of carboxylic acid anhydrides can significantly contribute to the cost of products. The typical method to generate vicinal diesters from epoxides using less expensive carboxylic acids involves acidic catalysis. However, the reaction of carboxylic acids with linoleic and linolenic acid epoxides under acidic conditions gives rise to the production of non-desired tetrahydrofuranic (THF) diesters. The acid-catalyzed reaction of linoleic acid ester diepoxides with carboxylic acids to produce THF diesters is shown below:

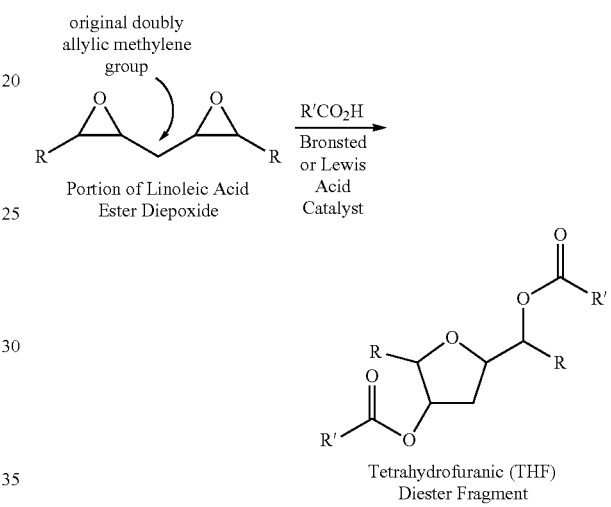

THF diesters are non-desired since they are prone to oxidation at both methine sites adjacent to the THF ring oxygen atom.

It would be desirable to provide improved methods and improved fatty acid compositions for preparing triglycerides containing fatty acid vicinal diester functionality. It would further be desirable to provide triglycerides that are useful for preparing a variety of products, such as lubricants and other industrial oils, and that are resistant to air oxidation.

DETAILED DESCRIPTION OF THE PREFERRED EMBODIMENTS

The present invention provides improved methods for preparing triglycerides containing fatty acid vicinal diester functionality. In a first embodiment, a method according to the invention comprises:

(a) providing a triglyceride including fatty acids with epoxide groups;

(b) reacting the epoxide groups with carboxylic acid salts under basic conditions to produce a triglyceride including fatty acids with vicinal ester/alkoxides;

(c) protonating the vicinal ester/alkoxides to produce a triglyceride including fatty acids with vicinal ester/alcohols; and (d) reacting the vicinal ester/alcohols with carboxylic acids under acidic conditions to produce a triglyceride including fatty acids with vicinal diesters.

An example of this method as it is applied to a triglyceride including linoleic acid is shown below:

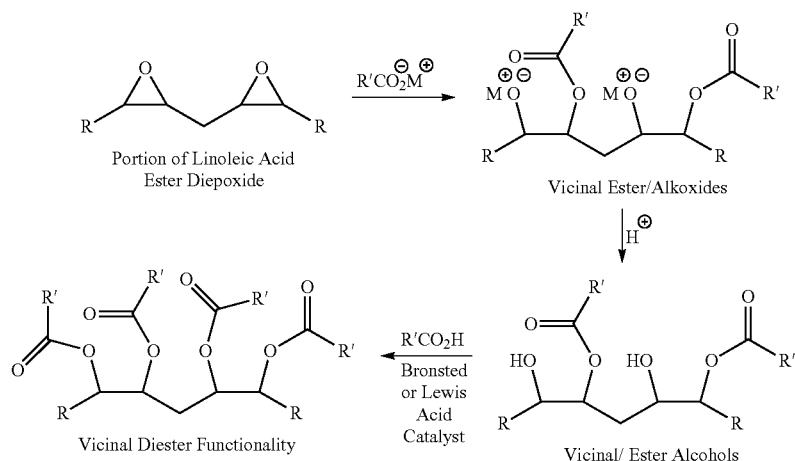

In this method, the formation of THF diesters is avoided in fatty acids containing double bonds (e.g., linoleic and linolenic acids) since their epoxides are not subjected to acidic conditions which trigger formation of THF diesters. In certain embodiments, the method minimizes production of fatty acids with THF diesters to less than 5 wt % of the total fatty acids, and preferably less than 1 wt %.

The reactivity of carboxylic acid salts in this approach is influenced by variations in ion-pairing between the carboxylate anion and the cation employed. Thus, the influences of various cations such as different alkali metals and quaternary ammonium salts on reaction efficiencies will be evaluated to determine the optimum cation and solvent to be used in this reaction sequence.

In a second embodiment, an improved method for preparing triglycerides containing fatty acid vicinal diester functionality comprises:

(a) providing a triglyceride including fatty acids with epoxide groups;

(b) reacting the epoxide groups with first carboxylic acids in the presence of a catalyst to produce a triglyceride including fatty acids with vicinal ester/alcohols; and (c) reacting the vicinal ester/alcohols with second carboxylic acids under acidic conditions to produce a triglyceride including fatty acids with vicinal diesters.

An example of this method as it is applied to a triglyceride including linoleic acid is shown below:

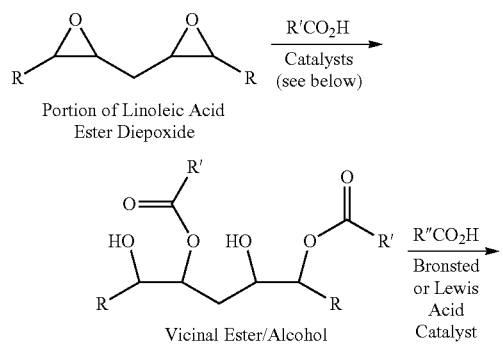

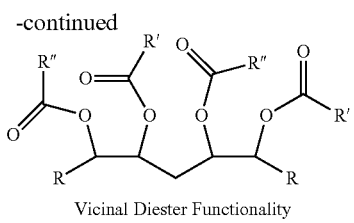

Vicinal Diester Functionality

Catalysts:
Tertiary amines
Tertiary phosphines
Quaternary ammonium
or Phosphonium salts This reaction scheme affords a number of advantages. There is no need to basify and then acidify reaction mixtures. The method can produce vicinal esters with the same or different vicinal ester groups (different groups typically leading to desired lower pour points).

Any suitable catalyst can be used in the first reaction. For example, some categories of catalysts that may be used include tertiary amines, tertiary phosphines, and quaternary ammonium or phosphonium salts. In certain embodiments, the first reaction is also heated.

Again, the formation of THF diesters is avoided in fatty acids containing double bonds.

The present invention also provides improved fatty acid compositions for preparing triglycerides containing fatty acid vicinal diester functionality. When introducing vicinal diester functionality to unsaturated fatty acids containing relatively low percentages of linoleic and linolenic acids (e.g., total of linoleic and linolenic less than 30 wt % of the total fatty acids, and preferably less than 20 wt %) and relatively high amounts of oleic acid (e.g., more than 40 wt % of the total fatty acids, and preferably more than 50 wt %), production of THF diesters can be minimized in two ways. One approach is to use the suggested approach involving reaction of their epoxides with carboxylic acid salts under initial basic conditions as described above.

Another approach is to utilize the reaction of their epoxides with carboxylic acids under acidic conditions. In this approach, the small amounts of THF diesters that would be formed may not adversely influence the performance of vicinal diester type triglycerides. If desired, these triglycerides can be formulated with small amounts of anti-oxidants to prevent THF diester oxidation.

In certain products, for example lubricants, there is a need for triglycerides having ISO viscosities in the 40-80 centistoke range. The ISO viscosities of vicinal diester type triglycerides are directly dependent on their linoleic acid/oleic acid ratios whereby the greater this ratio, the higher their ISO viscosities. Thus, vicinal diester type triglycerides derived from commodity oils such as soybean oils, that have relatively high linoleic acid/oleic acid ratios, have relatively high ISO viscosities. Hence, using fatty acids containing high percentages of oleic acid will facilitate preparation of decreased ISO viscosity triglycerides.

Another desired characteristic of vicinal diester-containing triglycerides in certain products, for example lubricants, is that they have pour points that are as low as possible, for example less than −5° C. Pour points in these type triglycerides are inversely dependent on the quantity of saturated fatty acids having more than 14 carbon atoms. Thus, preferred fatty acid compositions are those that also contain minimal amounts of saturated fatty acids having more than 14 carbon atoms (e.g., less than 10 wt % of the total fatty acids, and preferably less than 5 wt %).

Fatty acids possessing this combination of desired compositional properties may conveniently be derived from algal sources. However, they can also be derived from other renewable feedstocks.

In summary, to prepare triglycerides containing vicinal diester functionality derived from fatty acids containing a range of linoleic and linolenic acids and not generate THF diester functionality, the present invention provides a reaction sequence that starts with the reaction of fatty acid epoxides with relatively non-expensive carboxylic acid salts under basic conditions. Alternatively, triglycerides containing vicinal diester functionality can be prepared from fatty acids contain low to nil amounts of linoleic and linolenic acid by reacting fatty acid epoxides with carboxylic acids under basic or acidic conditions. Fatty acids containing low quantities of saturated fatty acids are also desired starting materials to produce vicinal diester-based triglycerides with low pour points.

The triglycerides produced according to the invention may be useful for preparing a wide variety of different products. In certain embodiments, the products are industrial fluids. The industrial fluids may be useful as engine oils (typically two cycle, four cycle, Wankel, and turbine type engines), hydraulic fluids, drive oils, metal working fluids, greases, general lubricants, brake fluids rock drilling fluid and the like.

The industrial fluids can contain another functional component in addition to the modified triglyceride of the invention. For example, the functional component may be selected from the group consisting of pour point depressant, anti-wear additive, base stock, diluent, extreme pressure additive, and antioxidant.

The invention claimed is:

1. A method for producing a triglyceride including fatty acids with vicinal diesters, the method comprising:
   (a) providing a triglyceride including fatty acids with epoxide groups;
   (b) reacting the epoxide groups with carboxylic acid salts under basic conditions to produce a triglyceride including fatty acids with vicinal ester/alkoxides;
   (c) protonating the vicinal ester/alkoxides to produce a triglyceride including fatty acids with vicinal ester/alcohols; and
   (d) reacting the vicinal ester/alcohols with carboxylic acids under acidic conditions to produce a triglyceride including fatty acids with vicinal diesters.

2. The method according to claim 1, wherein the method minimizes production of fatty acids with tetrahydrofuranic diesters to less than 5 wt % of the total fatty acids.

3. The method according to claim 1, wherein the fatty acids with epoxide groups of (a) include linoleic acids and linolenic acids of which double bonds have been epoxidized.

4. The method according to claim 1, wherein the carboxylic acid salts of (b) include a cation which is an alkali metal or a quaternary ammonium salt.

5. The method according to claim 1, wherein the triglyceride of (a) is an epoxidized soybean oil or an epoxidized algal oil.

6. The method according to claim 1, wherein the product triglyceride of (d) has an ISO viscosity within a range of 40-80 centistokes.

7. The method according to claim 6, wherein the triglyceride of (a) is an epoxidized triglyceride including less than 30 wt % total linoleic and linolenic fatty acids and more than 40 wt % oleic fatty acids.

8. The method according to claim 1, wherein the product triglyceride of (d) has a pour point less than −5° C.

9. The method according to claim 8, wherein the triglyceride of (a) is an epoxidized triglyceride including less than 10 wt % saturated fatty acids having more than 14 carbon atoms.

* * * * *